(12) United States Patent
Druy et al.

(10) Patent No.: US 6,289,149 B1
(45) Date of Patent: Sep. 11, 2001

(54) FIBER OPTIC COUPLED TRANSMISSION CELL FOR IN-PROCESS SPECTROGRAPHIC ANALYSIS

(75) Inventors: Mark A. Druy, Arlington; Paul J. Glatkowski, Littleton; Lawrence E Curtiss, Concord, all of MA (US)

(73) Assignee: Foster-Miller, Inc., Waltham, MA (US)

( * ) Notice: Subject to any disclaimer, the term of this patent is extended or adjusted under 35 U.S.C. 154(b) by 0 days.

(21) Appl. No.: 09/230,029

(22) PCT Filed: Apr. 30, 1997

(86) PCT No.: PCT/US97/07320

§ 371 Date: Jan. 19, 1999

§ 102(e) Date: Jan. 19, 1999

(87) PCT Pub. No.: WO97/41470

PCT Pub. Date: Nov. 6, 1997

Related U.S. Application Data

(60) Provisional application No. 60/016,558, filed on Apr. 30, 1996.

(51) Int. Cl.$^7$ .............................. G02B 6/32; G01N 21/01
(52) U.S. Cl. ................... 385/31; 385/73; 385/74; 385/75; 385/33; 385/900
(58) Field of Search .......................... 385/33–34, 900, 385/31, 53, 56, 58, 60, 70, 72, 73, 74, 75; 356/406, 328, 244, 246

(56) References Cited

U.S. PATENT DOCUMENTS

| | | | |
|---|---|---|---|
| 4,496,787 | * 1/1985 | Touchais et al. | 136/248 |
| 5,477,322 | * 12/1995 | Malinen | 356/328 |
| 6,163,641 | * 12/2000 | Eastgate | 385/125 |
| 6,219,140 | * 4/2001 | Kaplan | 356/406 |

* cited by examiner

Primary Examiner—Frank G. Font
Assistant Examiner—Michael P Mooney
(74) Attorney, Agent, or Firm—Perkins, Smith & Cohen, LLP; Stephen Y. Chow

(57) ABSTRACT

A transmission cell apparatus for in-process spectroscopy comprising symmetric compound parabolic light concentrators (4, 5) terminating optical transmission fibers (8, 9) and abutting windows (2, 3) defining the sample cell.

9 Claims, 3 Drawing Sheets

FIBER OPTIC COUPLED TRANSMISSION CELL FOR IN-PROCESS SPECTROGRAPHIC ANALYSIS

This application is filed as an International Application with the United States Patent and Trademark Office as a Receiving Office, designating the United States as one country, and claims priority of a provisional application entitled "Fiber Optic Coupled Transmission Cell" filed Apr. 30, 1996, in the United States Patent and Trademark Office, Ser. No. 60/016,558.

FIELD OF THE INVENTION

The field of the invention is spectroscopy, in particular, infrared spectroscopy.

BACKGROUND OF THE INVENTION

Infrared (IR) spectroscopy typically involves the transmission of light of a range of infrared frequencies through a sample, resulting in the detection of the absorption of certain frequency components by certain materials thereby indicating the presence of those components in the sample. It has been found that a "mid-IR" range of frequencies, corresponding to 2.5–25 microns in wavelength or 4000–400 in wavenumbers, is particularly useful for analyses of oils, lubricants, and beverages, particularly dairy products.

Remote infrared spectroscopic monitoring using optical fibers is useful in spectroscopy, as discussed, for example, in U.S. Pat. No. Re. 33,789 to Stevenson, U.S. Pat. No. 5,076,243 to Bornstein, U.S. Pat. No. 5,239,176 to Stevenson, U.S. Pat. No. 4,852,967 to Cook, and U.S. Patent No. 5,585,634 to Stevenson et al. The material being analyzed or monitored may be gaseous, liquid, or solid, and sampling may be readily performed outside the sample compartment of a conventional spectrometer thus permitting in situ, real-time spectroscopic measurements and eliminating the need to transport a sample to the spectrometer.

The components for a transmitting light in the mid-IR through a traditional transmission cell containing a sample are expensive, including expensive antireflection-coated germanium/zinc selenide lenses to collimate the light directed to the sample and the light transmitted from the sample. Moreover, such components are difficult to handle, requiring relatively precise alignment, but being prone to scratching and breaking.

Other solutions such as the use of parabolic mirrors also required relatively precise alignment, which presented problems in an industrial process environment where mid-IR spectroscopy can be put to good use.

Non-imaging concentrators, comprising highly reflective internal conical or compound parabolic surfaces have been used to collimate IR light in spectroscopy, for example, the "System Having Non-Imaging Concentrators for Performing IR Transmission Spectroscopy," disclosed in U.S. Pat. No. 5,254,858, issued Oct. 19, 1993, to Wolfman et al. That system, however, calls for the use of two concentrators tapered towards each other to collimate a light source and does not appear adapted to an in-process configuration.

SUMMARY OF THE INVENTION

The invention, specifically adapted to an environment of samples taken in-process with varying viscosities and at various pressures, is a structure enclosing a sample cell, defined further by parallel infrared transmitting windows, through which sample fluid is circulated, and symmetric compound parabolic, concentrators abutting each of the parallel infrared transmitting windows at the wider ends of the concentrators. Fiber optic cables are connected to the narrower ends of the concentrators to an optical connection to a light source and detector. Ingress and egress fittings are provided in the structure to allow the input and output of the sample fluid.

In a preferred embodiment, one or more circumferential channels are provided in the cell cavity to facilitate circulation of more viscous sample fluids. Shafts in the structure may be provided to accommodate heating elements and a temperature sensor. Thus, the invention provides a robust and modular structure that is well suited for in-process use in industrial processes.

It has been found that the invention not only enjoys a significant cost advantage over the traditional lens approach, but performs 10-100 times better in the mid-IR region in terms of definition of percentage transmission of relevant absorption peaks. It has also been found that the invention does not suffer from interference patterns (manifested as "wiggles") observed in the lens approach. Other advantages will be apparent from the detailed description and drawings.

DETAILED DESCRIPTION OF THE DRAWINGS

Figure 1:
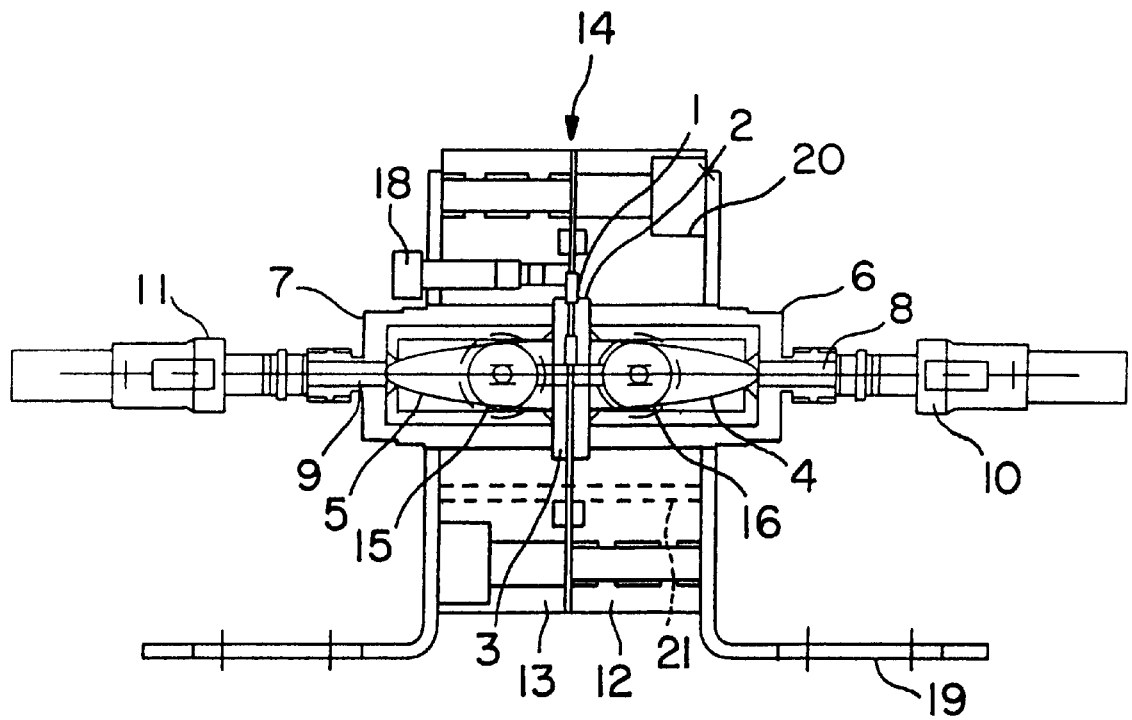
FIG. 1 shows a cross-sectional side view of the assembled transmission cell of the invention.

FIG. 1 shows a cross-sectional side view of the invention, assembled in a structure comprising two cell housing halves 12 and 13. Each may be fabricated from stainless steel in a cylindrical block with appropriate recesses and apertures milled and drilled, such as apertures 15 and 16 for ingress and egress of sample fluid (disposed on opposite sides in the assembled state). The housing halves may be held together using bolts, engaging, for example, female fitting 20. The entire structure may be based on bracket 19.

The two cell housing halves are separated by spacing material 14, which may include a membrane or o-ring or both. The spacing defines a cell path length, of the order of approximately 40–400 microns, between parallel transmission windows 2 and 3, which may comprise zinc selenide, barium fluoride, or diamond. The windows are fitted (and may be glued) in a recesses in the housing halves.

Coupler housings 6 and 7 support substantially symmetric concentrators 4 and 5 respectively, fitted (preferably by threading) in cell housing halves 12 and 13 respectively, and bringing the wider end of concentrators 4 and 5 in contact with windows 2 and 3 respectively. Concentrators 4 and 5 are preferably "compound parabolic concentrators," that is, parabolas or half-ellipses of revolution. Coupler housings 6 and 7 also include optical fibers 8 and 9 terminating at the narrower ends of concentrators 4 and 5 respectively. The optical fibers 8 and 9 may be extended from optical fiber cable connectors 10 and 11 respectively.

In operation, IR light of a range of frequencies may be guided from a light source (not shown) through optical fiber 8, collimated in concentrator 4, and transmitted through window 2 into the sample space between windows 2 and 3. Sample fluid may be input through aperture 16, and circulated within the sample space with the help of channel 17, then output through aperture 15. The IR light transmitted through window 2 is transmitted through the sample fluid, which selectively absorbs some of the light. The unabsorbed IR spectrum is then transmitted through window 3, collected in concentrator 5 and output through optical fiber 9 connected to a detector (not shown). In this embodiment either the flow of sample fluid or the transmission of light or both may be reversed in direction.

Figure 2:
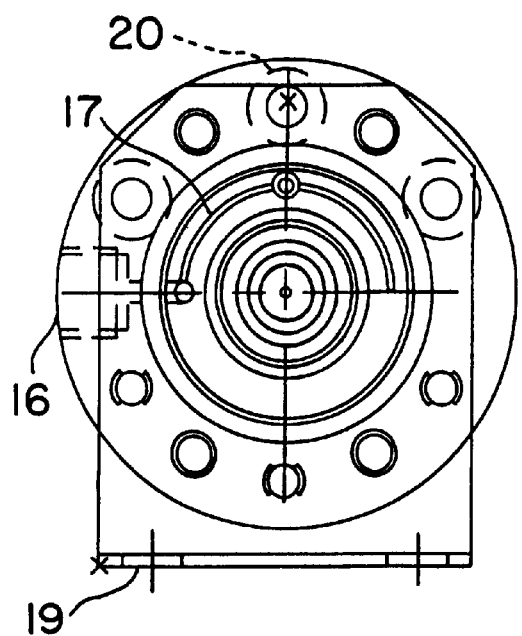
FIG. 2 shows a plan view of one half of the cell assembly, showing the circumferential channel of a preferred embodiment.

FIG. 2 shows a plan view of cell housing half 12, with ingress/egress aperture 16 for sample fluid connected to a circumferential channel 17 for circulating sample fluid within the space between the assemble cell housing halves 12 and 13 further defined by spacer 14 and transmission windows 2 and 3. An optional valve 18 may be provided to control the flow. Heating elements (not shown) and a temperature sensor such as a thermocouple (not shown) may be inserted in shafts as exemplified by shaft 21.

Figure 3:
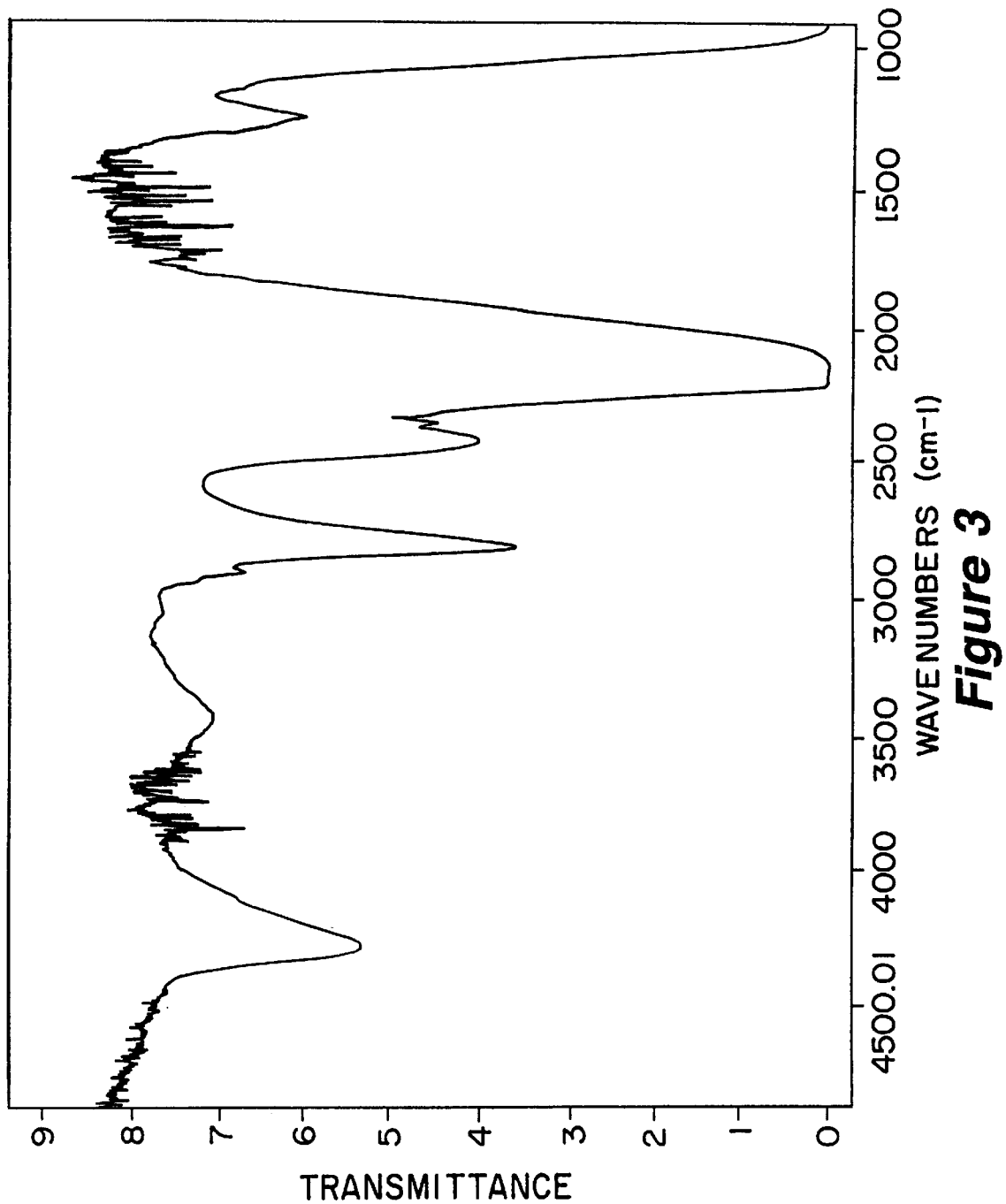
FIG. 3 shows the transmission spectrum of infrared radiation through the cell.

FIG. 3 shows a plot of the transmission of infrared radiation through a 19 mm (window diameter) cell with barium fluoride windows, indicating that about 9% of the energy in the sample compartment is transmitted through the optical fibers and cell structure.

Figure 4:
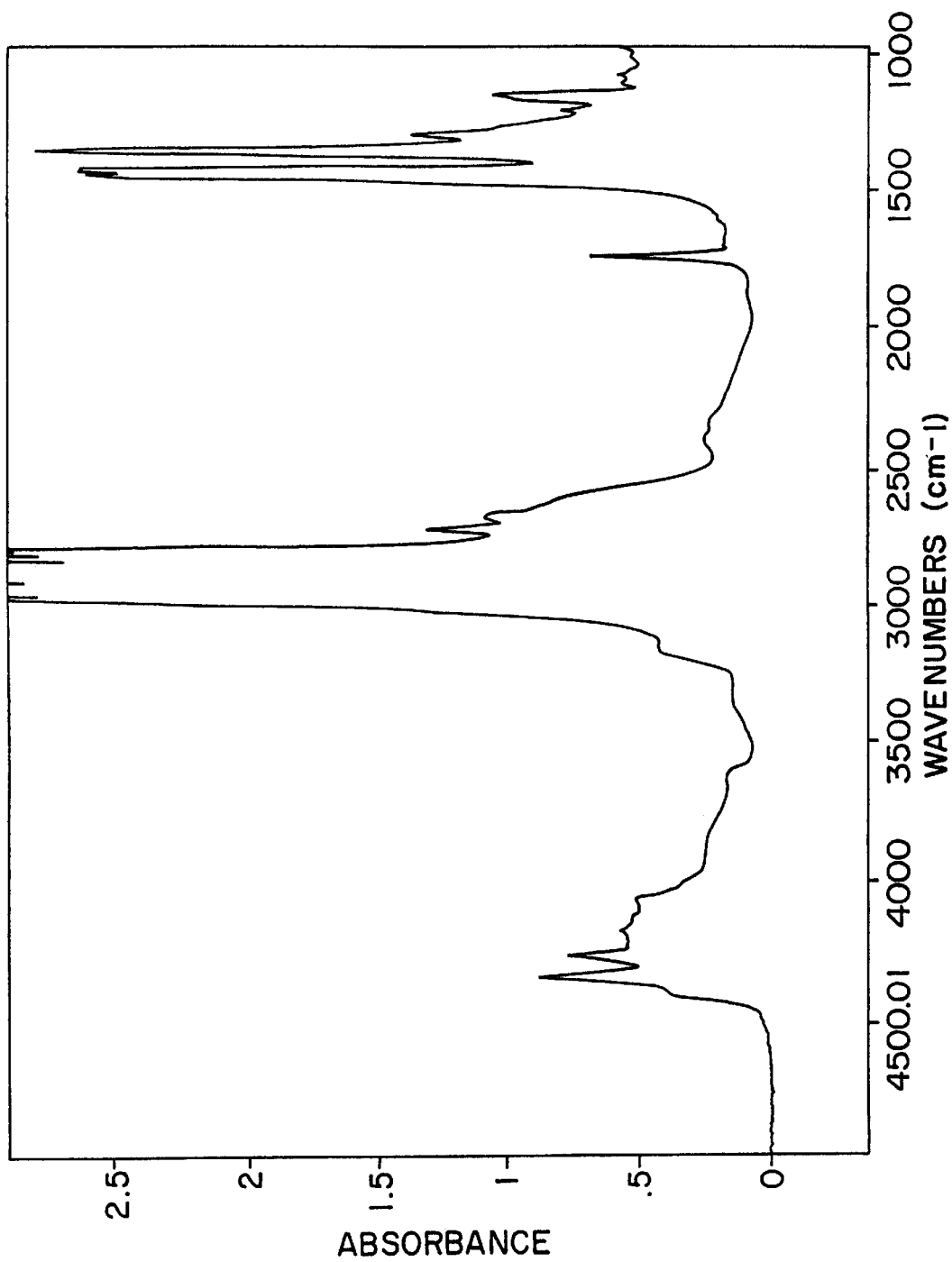
FIG. 4 shows the infrared absorption spectrum of an oil that is resident in the pathlength of the cell.

FIG. 4 shows the infrared absorption spectrum of an oil placed in the cell space of the above implementation.

We claim:
1. An apparatus for transmitting light through a sample comprising:
   a) a housing supporting a pair of parallel windows with a space therebetween in which said sample is placed; and
   b) a pair of symmetric light concentrators with narrower and wider ends disposed such that (I) said wider ends each abut one of said parallel windows opposite said sample space and (ii) said narrower ends each terminate an optical transmission fiber.
2. The apparatus of claim 1 wherein said housing provides ingress and egress ports in fluid communication with said space between said parallel windows f o r circulation of sample fluids there through.
3. The apparatus of claim 2 further comprising at least one circumferential channel for facilitating said circulation.
4. The apparatus of claim 1 further comprising a fitting for a heating element.
5. The apparatus of claim 1 wherein said symmetric light concentrators are compound parabolic concentrators.
6. The apparatus of claim 1 wherein said symmetric light concentrators are conical concentrators.
7. The apparatus of claim 1 wherein said windows are zinc selenide.
8. The apparatus of claim 1 wherein said windows are barium fluoride.
9. The apparatus of claim 1 wherein said windows are diamond.

* * * * *